(12) United States Patent
Mossman

(10) Patent No.: US 8,164,044 B2
(45) Date of Patent: Apr. 24, 2012

(54) WATERTIGHT CONNECTION SYSTEM FOR COMBINED ELECTRICAL AND FIBER OPTIC CABLES

(76) Inventor: Guy E. Mossman, Mt. Pleasant, SC (US)

( * ) Notice: Subject to any disclaimer, the term of this patent is extended or adjusted under 35 U.S.C. 154(b) by 0 days.

(21) Appl. No.: 12/591,913

(22) Filed: Dec. 4, 2009

(65) Prior Publication Data
US 2010/0079759 A1    Apr. 1, 2010

Related U.S. Application Data

(60) Division of application No. 11/822,475, filed on Jul. 6, 2007, now Pat. No. 7,781,725, which is a continuation of application No. 10/968,975, filed on Oct. 21, 2004, now abandoned.

(60) Provisional application No. 60/512,783, filed on Oct. 21, 2003.

(51) Int. Cl.
*G01J 1/04* (2006.01)
(52) U.S. Cl. .................. 250/227.16; 73/73; 250/227.11; 385/55

(58) Field of Classification Search ............. 250/227.16, 250/227.11; 385/55; 73/73
See application file for complete search history.

(56) References Cited

U.S. PATENT DOCUMENTS

| | | | |
|---|---|---|---|
| 4,616,900 A * | 10/1986 | Cairns ............................ | 385/73 |
| 6,295,394 B1 * | 9/2001 | Arab-Sadeghabadi ......... | 385/12 |
| 6,753,520 B2 * | 6/2004 | Spirin et al. ............. | 250/227.16 |
| 2003/0016916 A1 * | 1/2003 | Allen et al. ..................... | 385/55 |
| 2004/0114888 A1 * | 6/2004 | Rich et al. ..................... | 385/101 |
| 2005/0123230 A1 * | 6/2005 | Twerdochlib ................... | 385/12 |

* cited by examiner

*Primary Examiner* — Georgia Epps
*Assistant Examiner* — Kevin Wyatt
(74) *Attorney, Agent, or Firm* — Merek, Blackmon & Voorhees, LLC

(57) ABSTRACT

A connector apparatus for use with combined electrical and fiber optic cables in wet or undersea conditions. The connector apparatus includes an outer threaded male connector portion connected to a first cable and a compatible female connector portion having a rotating internally threaded collar for engaging the outer male connector portion. The female connector portion includes conductor pins and a fiber-optic terminal pin and a fiber optic sensor ring.

3 Claims, 2 Drawing Sheets

_US 8,164,044 B2_

WATERTIGHT CONNECTION SYSTEM FOR COMBINED ELECTRICAL AND FIBER OPTIC CABLES

EARLIER FILED APPLICATIONS

This application is a divisional of U.S. patent application Ser. No. 11/822,475 filed Jul. 6, 2007 now U.S. Pat. No. 7,781,725 which is a continuation of U.S. patent application Ser. No. 10/968,975 filed Oct. 21, 2004 now abandoned and also claims priority from provisional application Ser. No. 60/512,783 filed on Oct. 21, 2003. Applicant claims the benefit of the filing date of all earlier filed applications and incorporates these applications herein by reference.

FIELD OF THE INVENTION

The present invention relates to a connector for use with a combined electrical and fiber optic cable in wet or undersea environments.

BACKGROUND OF THE INVENTION

Keeping electrical and optical fiber connections watertight is important for the operation of electrical and optical systems. In electrical systems water ingress can cause a short circuit and interrupt the electrical signal. Even if the short circuit does not occur immediately, moisture and particularly saltwater can cause corrosion, which over time will cause degradation of the electrical connection. In optical systems, water can degrade the light traveling through the optical fibers and disrupt the accuracy of the signal.

In view of the foregoing it can be seen that there is a need for an improved connector for use with combined electrical and optical fiber connections in wet and/or undersea conditions.

OBJECTS AND SUMMARY OF THE INVENTION

An object of the invention is to provide an electric cable connector having an optical fiber for use in determining that the connection is watertight.

Another object of the invention is to provide a connector having an opening for receiving an optical fiber Yet another object of the invention is to provide a rotating collar for connecting a portion of the watertight connector to a second portion of the watertight connector to join two combined electrical cables;

Still another object of the invention is to provide a connecter having connections for facilitating the fiber optic cable connection.

In summary, the invention is to a connector apparatus for use with an electrical cable and an optical fiber in wet or undersea conditions to facilitate testing of the connector. The connector apparatus preferably includes an outer threaded male connector portion connected to a first cable and a compatible female connector portion having a rotating internally threaded collar for engaging the outer male connector portion. The female connector portion includes conductor pins and a fiber-optic terminal pin and a fiber optic sensor ring. When water or moisture is present in the connector, it is detected by determining the light output of the fiber optic sensor compared against a baseline light output signal.

DETAILED DESCRIPTION OF THE PREFERRED EMBODIMENT

Figures 1, 2:
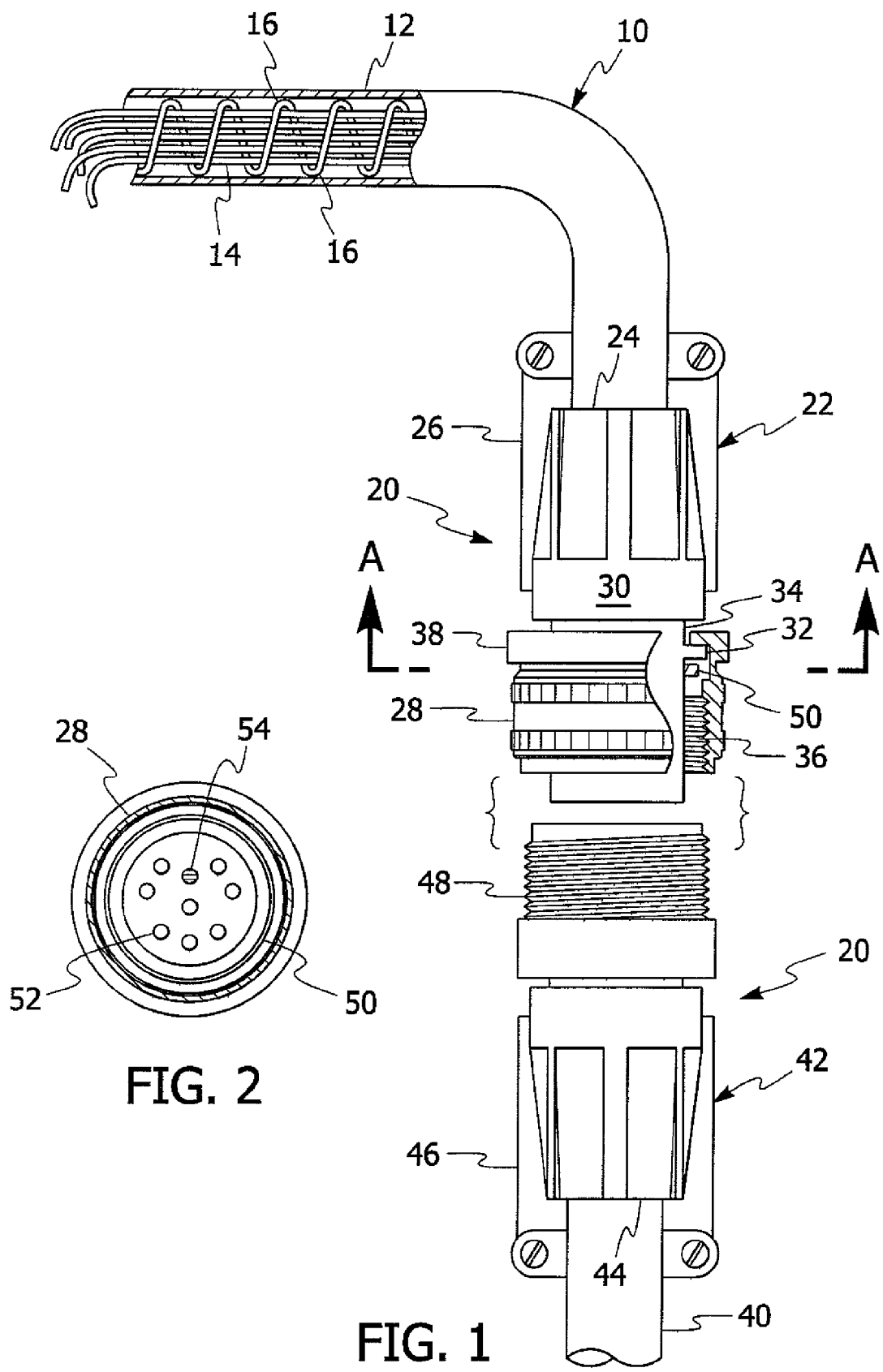
FIG. 1 is a top plan view of the connector assembly.
FIG. 2 is a sectional view of the connector assembly of FIG. 1 taken along lines A-A; and,
FIG. 3 is a top plan view of another embodiment of the connector assembly with portions broken away.

A combination electrical and fiber optic cable 10 is shown in FIG. 1. The cable 10 includes a cable jacket 12 which is preferably insulated and encasing conventional electric wire strands 14 and fiber optic sensor strand 16. In the preferred embodiment, the fiber optic sensor strand 16 helically encircles the electric wire strands 14, however the optical fiber 16 could also be separate from the cable 10.

The cable 10 is joined to connector 20. Connector 20 includes a female portion 22 having an opening 24 for receiving the cable 10. Female portion 22 includes an elongated housing 26 extending from opening 24 to an internally threaded rotating collar 28. Housing 26 includes a shoulder portion 30 spaced from a step 32 and forming a channel 34 extending circumferentially around the housing 26. The collar 28 includes an internally threaded ring 36 and a flange 38 extending into the channel 34 wherein shoulder 30 and step 32 limit movement of the collar 28 along the housing 26.

A second combination electrical and fiber optic sensor strand 40 is joined to connector 20. Connector 20 includes a male portion 42 having an opening 44 for receiving the strand 40. Male portion 42 includes an elongated housing 46 extending from the opening 44 to an externally threaded portion 48 which is sized to be received within the collar 28.

FIG. 2 shows a cross-section taken along lines A-A and illustrates the rotating collar 28, the fiber optic sensor ring 50, the electrical conductor pins 52 and the fiber optic terminal pin 54.

Preferably, the connector 20 is formed of corrosion resistant material such as plastic or stainless steel.

Figure 3:
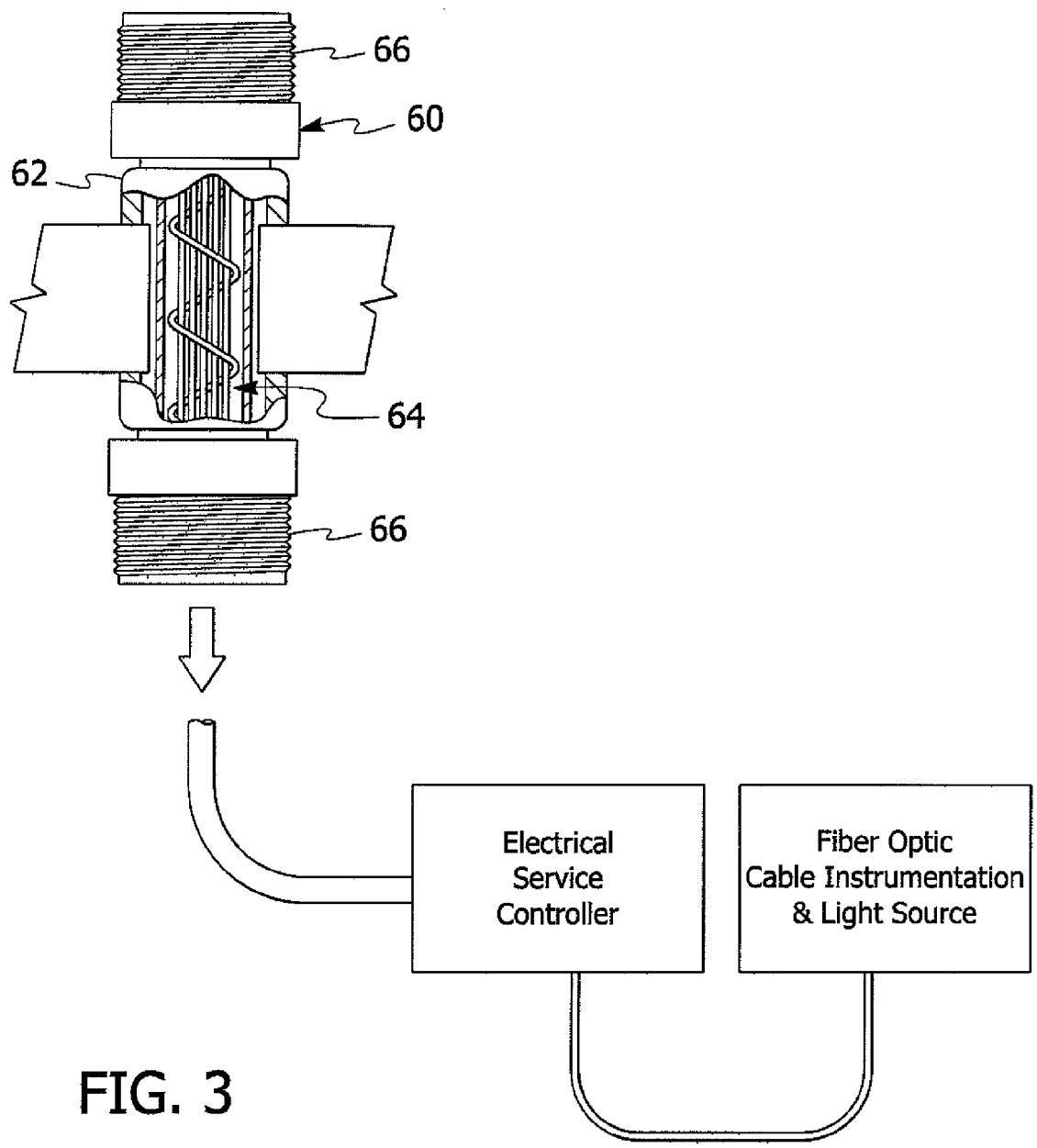

FIG. 3 is an alternative embodiment for use in through hull or deck fittings. An elongated connector 60 is shown having a conduit 62 for surrounding the combination electrical and fiber optic sensor strand 64. A threaded connector 66 is located at each end of the conduit 62. It should be understood by those skilled in the art that the conduit 62 could be any length as necessary and that the threaded connectors 66 could be externally threaded as shown, but also one or both could be internally threaded.

In operation in the first embodiment, light is transmitted through the fiber optic sensor strand 16 to the fiber optic sensor ring 50 and then through strand 40 and the light output is detected and compared to a predetermined value taken when the connector 20 is known to be dry. If the light output is degraded then the connector 20 should be checked for moisture or corrosion. The through-hull elongated connector 60 of the alternative embodiment would be tested in the same manner.

While this invention has been described as having a preferred design, it is understood that it is capable of further modifications, uses and/or adaptations of the invention following in general the principle of the invention and including such departures from the present disclosure as come within the known or customary practice in the art to which the invention pertains and as maybe applied to the central features hereinbefore set forth, and fall within the scope of the invention and the limits of the appended claims.

I claim:
1. A combined electrical and fiber optic sensor strand connector assembly comprising:
 a) said connector assembly having a male portion and a female portion;

b) said male portion of said connector assembly having a watertight cable receiving opening at a first end and an externally threaded connection opening at a second end;
c) said female portion of said connector assembly having a watertight cable receiving opening at a first end and an internally threaded rotatable sleeve at a second end;
d) a first combined electrical and fiber optic sensor strand being attached to said male portion and a second combined electrical and fiber optic sensor strand being attached to said female portion so that when said male portion is connected to said female portion said first and second combined electrical and fiber optic sensor strands are electrically connected;
e) at least one of said male portion and said female portion having a sensor ring connected to said fiber optic sensor strand for detecting the presence of moisture within said connector assembly.

2. The combined electrical and fiber optic sensor strand connector assembly as set forth in claim 1, wherein:
a) the presence of moisture is detected by transmitting light through said optic sensor strand and light output through said sensor ring is compared to a predetermined value.

3. A method of detecting moisture in a connector assembly having male portion and a female portion wherein said male portion of said connector assembly having a watertight cable receiving opening at a first end and an externally threaded connection opening at a second end and said female portion of said connector assembly having a watertight cable receiving opening at a first end and an internally threaded rotatable sleeve at a second end and a first combined electrical and fiber optic sensor strand being attached to said male portion and a second combined electrical and fiber optic sensor strand being attached to said female portion so that when said male portion is connected to said female portion said first and second combined electrical and fiber optic sensor strands are electrically connected wherein at least one of said male portion and said female portion having a sensor ring connected to said fiber optic sensor strand, comprising the steps of:
a) transmitting light through at least one of said sensor strands to said sensor ring;
b) detecting the light passing through said sensor ring; and,
c) measuring the light passing through said sensor ring against a predetermined value.

* * * * *